United States Patent
Briman

(10) Patent No.: US 10,261,047 B2
(45) Date of Patent: Apr. 16, 2019

(54) CARTRIDGE FOR DIAGNOSTIC TESTING

(71) Applicant: Proxim Diagnostics Corporation, Mountain View, CA (US)

(72) Inventor: Mikhail Briman, San Jose, CA (US)

(73) Assignee: Proxim Diagnostics Corporation, Mountain View, CA (US)

( * ) Notice: Subject to any disclaimer, the term of this patent is extended or adjusted under 35 U.S.C. 154(b) by 0 days.

(21) Appl. No.: 16/023,759

(22) Filed: Jun. 29, 2018

(65) Prior Publication Data

US 2018/0313788 A1 Nov. 1, 2018

Related U.S. Application Data

(60) Continuation of application No. 15/469,275, filed on Mar. 24, 2017, now Pat. No. 10,036,726, which is a
(Continued)

(51) Int. Cl.
*G01N 27/49* (2006.01)
*G01N 27/48* (2006.01)
(Continued)

(52) U.S. Cl.
CPC ............ *G01N 27/49* (2013.01); *B01L 3/5027* (2013.01); *B01L 3/502707* (2013.01); *G01N 27/3272* (2013.01); *G01N 27/48* (2013.01); *G01N 33/5438* (2013.01); *G01N 33/6893* (2013.01); *B01L 2200/16* (2013.01); *B01L 2300/0645* (2013.01); *B01L 2300/0672* (2013.01);
(Continued)

(58) Field of Classification Search
CPC ............... G01N 27/48; G01N 33/5438; G01N 33/54386; B01L 3/5027; B01L 3/502715; B01L 2300/064; B01L 2300/0663; B01L 2300/0816
See application file for complete search history.

(56) References Cited

U.S. PATENT DOCUMENTS 4,554,064 A    11/1985   McClintock et al.
5,096,669 A    3/1992    Lauks et al.
(Continued)

FOREIGN PATENT DOCUMENTS

WO    WO96/22730 A1    8/1996
WO    WO01/42473 A2    6/2001
(Continued)

OTHER PUBLICATIONS

Alwarappan et al.; Probing the electrochemical properties of graphene nanosheets for biosensing applications; J. Phys. Chem.; 113(20); pp. 8853-8857; Apr. 2009.
(Continued)

*Primary Examiner* — Brian R Gordon
(74) *Attorney, Agent, or Firm* — Shay Glenn LLP

(57) ABSTRACT

The present invention relates to a cartridge for conducting diagnostic assays. The cartridge consists of an assembly of components that are easily assembled. The cartridge provides means for receiving a patient sample, precisely controlling fluid introduction, onboard storage of assay fluid and conducting different assay protocols and detection of a plurality of analytes. Methods of use for the cartridge are described. The disclosed invention is suitable for point of care environments or any place where rapid, ultrasensitive testing is required.

31 Claims, 7 Drawing Sheets

Related U.S. Application Data division of application No. 14/233,008, filed as application No. PCT/US2011/053535 on Sep. 27, 2011, now Pat. No. 9,638,663.

(60) Provisional application No. 61/511,514, filed on Jul. 25, 2011.

(51) Int. Cl.
| | |
|---|---|
| *G01N 33/543* | (2006.01) |
| *G01N 3/00* | (2006.01) |
| *G01N 33/68* | (2006.01) |
| *G01N 27/327* | (2006.01) |
| *B01L 3/00* | (2006.01) |

(52) U.S. Cl.
CPC ........ *B01L 2300/0681* (2013.01); *B01L 2300/0816* (2013.01); *B01L 2300/0867* (2013.01); *B01L 2300/0883* (2013.01); *B01L 2300/161* (2013.01); *B01L 2400/0478* (2013.01); *B01L 2400/0487* (2013.01); *B01L 2400/0638* (2013.01); *B01L 2400/0655* (2013.01); *B01L 2400/0683* (2013.01); *B01L 2400/0694* (2013.01); *G01N 2333/4712* (2013.01); *G01N 2800/324* (2013.01)

(56) References Cited

U.S. PATENT DOCUMENTS

| | | | |
|---|---|---|---|
| 5,118,403 A | 6/1992 | Magee et al. |
| 5,120,420 A | 6/1992 | Nankai et al. |
| 5,324,400 A | 6/1994 | Eliash et al. |
| 5,399,256 A | 3/1995 | Bohs et al. |
| 5,624,597 A | 4/1997 | Buhl et al. |
| 5,628,890 A | 5/1997 | Carter et al. |
| 5,744,096 A | 4/1998 | Jones et al. |
| 5,834,220 A | 11/1998 | Wicks et al. |
| 6,123,820 A | 9/2000 | Bergkuist et al. |
| 6,251,684 B1 | 6/2001 | Buhl et al. |
| 6,342,347 B1 | 1/2002 | Bauer |
| 6,361,958 B1 | 3/2002 | Shieh et al. |
| 6,376,206 B1 | 4/2002 | Katus et al. |
| 6,426,230 B1 | 7/2002 | Feistel |
| 6,565,738 B1 | 5/2003 | Henning et al. |
| 6,576,461 B2 | 6/2003 | Heller et al. |
| 6,627,404 B1 | 9/2003 | Buechler et al. |
| 6,689,317 B1 | 2/2004 | Rees |
| 6,750,053 B1 | 6/2004 | Widrig Opalsky et al. |
| 6,845,327 B2 | 1/2005 | Lauks |
| 6,923,894 B2 | 8/2005 | Huang et al. |
| 7,202,042 B2 | 4/2007 | Buechler |
| 7,238,519 B2 | 7/2007 | Bellet et al. |
| 7,335,294 B2 | 2/2008 | Heller et al. |
| 7,419,821 B2 | 9/2008 | Davis et al. |
| 7,427,490 B2 | 9/2008 | Valkirs et al. |
| 7,476,360 B2 | 1/2009 | Gau et al. |
| 7,497,997 B2 | 3/2009 | Glezer et al. |
| 7,598,091 B2 | 10/2009 | Wang |
| 7,723,099 B2 | 5/2010 | Miller et al. |
| 7,771,583 B2 | 8/2010 | Diamond et al. |
| 7,842,234 B2 | 11/2010 | Lauks et al. |
| 7,906,009 B2 | 3/2011 | Heller et al. |
| 7,938,573 B2 | 5/2011 | Gau et al. |
| 8,083,927 B2 | 12/2011 | Wang et al. |
| 8,084,272 B2 | 12/2011 | Campbell et al. |
| 8,110,392 B2 | 2/2012 | Battrell et al. |
| 8,114,612 B2 | 2/2012 | Buechler et al. |
| 8,123,920 B2 | 2/2012 | Iyengar et al. |
| 8,152,991 B2 | 4/2012 | Briman et al. |
| 8,163,163 B2 | 4/2012 | Purvis |
| 8,273,566 B2 | 9/2012 | Billadeau et al. |
| 8,283,155 B2 | 10/2012 | Holmes et al. |
| 8,357,495 B2 | 1/2013 | Mattingly et al. |
| 8,367,398 B2 | 2/2013 | Lee et al. |
| 8,425,745 B2 | 4/2013 | Briman et al. |
| 8,506,908 B2 | 8/2013 | Benn et al. |
| 8,510,067 B2 | 8/2013 | Zelin et al. |
| 8,530,230 B2 | 9/2013 | Stromgren et al. |
| 8,591,817 B1 | 11/2013 | Gau |
| 8,591,829 B2 | 11/2013 | Taylor et al. |
| 8,691,592 B2 | 4/2014 | Chen et al. |
| 8,697,009 B2 | 4/2014 | Saltsman et al. |
| 8,747,747 B2 | 6/2014 | Hunter |
| 8,765,062 B2 | 7/2014 | Linder et al. |
| 8,765,075 B2 | 7/2014 | Miller et al. |
| 8,826,752 B2 | 9/2014 | Miller |
| 8,961,883 B2 | 2/2015 | Song et al. |
| 8,988,079 B2 | 3/2015 | Briman et al. |
| 9,000,769 B2 | 4/2015 | Briman |
| 9,144,419 B2 | 9/2015 | Poirier et al. |
| 9,234,867 B2 | 1/2016 | Briman et al. |
| 9,291,613 B2 | 3/2016 | Bryant et al. |
| 9,339,815 B2 | 5/2016 | Kim et al. |
| 9,638,663 B2 | 5/2017 | Briman |
| 10,036,726 B2 | 7/2018 | Briman |
| 10,041,900 B2 | 8/2018 | Briman |
| 2002/0114739 A1 | 8/2002 | Weigl et al. |
| 2003/0190608 A1 | 10/2003 | Blackburn |
| 2004/0002161 A1 | 1/2004 | Sin |
| 2005/0009101 A1 | 1/2005 | Blackburn |
| 2005/0118061 A1 | 6/2005 | Mototsu |
| 2005/0130296 A1 | 6/2005 | Pisharody et al. |
| 2005/0211559 A1 | 9/2005 | Kayyem |
| 2006/0046300 A1 | 3/2006 | Padmanabhan et al. |
| 2006/0166090 A1 | 7/2006 | Grigorian et al. |
| 2006/0205061 A1 | 9/2006 | Roukes |
| 2006/0275852 A1 | 12/2006 | Montagu et al. |
| 2007/0093704 A1 | 4/2007 | Brister et al. |
| 2007/0158618 A1 | 7/2007 | Song et al. |
| 2007/0263046 A1 | 11/2007 | Iwasa et al. |
| 2007/0284557 A1 | 12/2007 | Gruner et al. |
| 2008/0009002 A1 | 1/2008 | Gruner et al. |
| 2009/0030293 A1 | 1/2009 | Cooper et al. |
| 2009/0042280 A1 | 2/2009 | Yang et al. |
| 2009/0159464 A1 | 6/2009 | Hyland et al. |
| 2009/0169467 A1 | 7/2009 | Zhamu et al. |
| 2009/0169725 A1 | 7/2009 | Zhamu et al. |
| 2009/0253149 A1 | 10/2009 | Ahrens et al. |
| 2009/0305135 A1 | 12/2009 | Shi et al. |
| 2010/0075311 A1 | 3/2010 | Barrault et al. |
| 2010/0143194 A1 | 6/2010 | Lee et al. |
| 2011/0003313 A1 | 1/2011 | Mendel-Hartvig et al. |
| 2011/0045505 A1 | 2/2011 | Warthoe et al. |
| 2011/0201099 A1 | 8/2011 | Anderson et al. |
| 2011/0201312 A1 | 8/2011 | Peterson et al. |
| 2011/0220656 A1 | 9/2011 | Gau |
| 2012/0142019 A1 | 6/2012 | Miller |
| 2012/0142020 A1 | 6/2012 | Miller |
| 2012/0190128 A1 | 7/2012 | Nikbakht et al. |
| 2012/0231488 A1 | 9/2012 | Marshall et al. |
| 2012/0255860 A1 | 10/2012 | Briman et al. |
| 2012/0301896 A1 | 11/2012 | Wang et al. |
| 2013/0000378 A1 | 1/2013 | Martin et al. |
| 2013/0309778 A1 | 11/2013 | Lowe et al. |
| 2014/0017709 A1 | 1/2014 | Lowe et al. |
| 2014/0141484 A1 | 5/2014 | Campbell et al. |
| 2015/0190810 A1 | 7/2015 | Glezer et al. |
| 2016/0123947 A1 | 5/2016 | Briman et al. |

FOREIGN PATENT DOCUMENTS

| | | |
|---|---|---|
| WO | WO2004/061418 A2 | 7/2004 |
| WO | WO2011/071772 A2 | 6/2011 |

OTHER PUBLICATIONS

Anjo et al.; Electrochemical activation of carbon electrodes in base: Minimization of dopamine adsorption and electrode capacitance; Anal. Chem.; 61(23); pp. 2603-2608; Dec. 1989.

Beilby et al.; A pyrolytic carbon film electrode for voltammetry; Journal of Electroanalytical Chemistry and Interfacial Electrochemistry; 248(2); pp. 283-304; Jul. 1988.

(56) References Cited

OTHER PUBLICATIONS

Beilby et al.; Comparison of the pyrolytic carbon film electrode with the wax-impregnated graphite electrode; Anal. Chem.; 36(1); pp. 22-26; Jan. 1964.

Bleda-Martinez et al.; Electrochemical methods to enhance the capacitance in activated carbon/polyaniline composites (proof copy); Journal of The Electrochemical Society; 155(10); pp. A672-A678; Jul. 2008.

Dock et al.; A steady-state and flow-through cell for screen-printed eight-electrode arrays; Analytica chimica Acta; 531(2); pp. 165-172; Feb. 2005.

Engstrom; Electrochemical pretreatment of glassy carbon electrodes; Anal. Chem.; 54(13); pp. 2310-2314; Nov. 1982.

Fernandez-Sanchez et al.; AC voltammetric carbon paste-based enzyme immunosensors; Biosensors & Bioelectronics; 14(12); pp. 917-924; Feb. 29, 2000.

Hance et al.; Effect of glassy carbon pretreatment on background double-layer capacitance and adsorption of neutral organic molecules; Anal. Chem.; 59(1); pp. 131-134; Jan. 1987.

Lu et al.; Nanometal-decorated exfoliated graphite nanoplatelet based glucose biosensors with high sensitivity and fast response; ACS Nano; 2(9); pp. 1825-1832; Sep. 2008.

Maeda et al.; Modification of glassy carbon surfaces by anodic oxidation in 1-alkanols; in Novel Trends in Electroorganic Synthesis; Springer, Japan; pp. 157-160; © 1998.

Maeda et al.; Surface characterization of glassy carbon electrodes anodized in 1-alkanols by their wettability and capacitance; Chem. Pharm. Bull.; 44(12); pp. 2294-2299; Dec. 1996.

Maeda et al.; Voltammetric behaviors of dopamine and ascorbic acid at a glassy carbon electrode anodized in 1, ?-akanediol; Analytical Sciences; 11(6); pp. 947-922; Dec. 1995.

Mizutani et al.; Amperometric glucose sensor using glassy carbon electrode anodized in 1, 5-Pentanediol as the base transducer; IEEJ Japan; 119-E(11); pp. 554-559; Nov. 1999.

Nian et al.; Nitric acid modification of activated carbon electrodes for improvement of electrochemical capacitance; Journal of the The Electrochemical society; 149(8); pp. A1008-A1014; Jul. 2002.

Park et al.; Amperometric biosensor for determination of ethanol vapor; Biosensors and Bioelectronics; 10(6-7); pp. 587-594; Jan. 1, 1995.

Ranganathan et al.; Facile preparation of active glassy carbon electrodes with activated carbon and organic solvents; Anal. Chem.; 71(16); pp. 3574-3580; Aug. 1999.

Shan et al.; Direct electrochemistry of glucose oxidase and biosensing for glucose based on graphene; Anal. Chem.; 81(6); pp. 2378-2382; Mar. 2009.

Stulik; Activation of solid electrodes; Electroanalysis; 4(9); pp. 829-834; Oct. 1, 1992.

Tang et al.; Preparation, structure, and electrochemical properties of reduced graphene sheet films; Adv. Funct. Mater.; 19(17); pp. 2782-2789; Sep. 2009.

Wang et al; Application of graphene-modified electrode for selective detection of dopamine; Electrochemistry Communications; 11(4); pp. 889-892; Apr. 2009.

Wang et al; Electrochemical activation of screen-printed carbon strips; Analyst; 121(3); pp. 345-350; Mar. 1996.

Wang et al.; Enhancement of electrochemical properties of screen-printed carbon electrodes by oxygen plasma treatment; Electrochemica Acta; 54(21); pp. 4937-4943; Aug. 30, 2009.

Yee et al.; Disposable thick-film amperometric biosensor with multiple working electrodes fabricated on a single substrate; Sensors and Actuators B; 34(1-3); pp. 490-492; Aug. 1, 1996.

CARTRIDGE FOR DIAGNOSTIC TESTING

CROSS REFERENCE TO RELATED APPLICATIONS

This application is a continuation of U.S. patent application Ser. No. 15/469,275, filed Mar. 24, 2017, now U.S. Pat. No. 10,036,726 which is a divisional of U.S. patent application Ser. No. 14/233,008, filed Jan. 15, 2014, now U.S. Pat. No. 9,638,663, which is a 371 of International Application No. PCT/US2011/053535, filed Sep. 27, 2011, which claims the benefit of priority from U.S. Provisional Application No. 61/511,514, filed Jul. 25, 2011, each of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

The present invention relates to the field of medical devices. Specifically, the invention relates to a cartridge for use in in vitro diagnostic applications with an emphasis on testing in point of care settings. Further, the cartridge is actuated by a reader module, which together can rapidly perform multiple diagnostics assays per patient sample.

BACKGROUND

In vitro diagnostics, the ability to measure and monitor various biological related markers from patient samples, has continued to gain prominence as a valuable input for physician decision making. The majority of clinical diagnostic tests are performed in a centralized lab located in a hospital or through an outside testing service. This procedure often delays results and adds significant costs to the healthcare system. In particular, for certain critical bio-markers there is a pressing need for quantification in the ultrasensitive regime, analyte concentrations in the femtomolar range and below, combined with short assay times so that medical intervention can take place more efficiently.

Most large and expensive clinical laboratory machinery can fulfill the quantitation aspect of testing but cannot deliver attractive turnaround time, a portable format, and attractive economics. A small but capable system that could be operated by a skilled or unskilled user could drastically improve patient outcomes.

Mentioned in the art are various point of care test systems incorporating a consumable that contains sensors of types including but not limited to: electrochemical, lateral flow, fluorescent, chemiluminescent, magnetic etc. However, there remains a latent need for a test system with a consumable cartridge that provides a platform for more robust and flexible testing. This type of cartridge format would provide fast assay times, performance that meets or exceeds laboratory instrumentation, ability to conduct multiple assays, ability to conduct multiple protocols, all constructed from components made of inexpensive materials.

SUMMARY OF THE DISCLOSURE

The present invention describes a cartridge and methods for using said cartridge in order to conduct multiple diagnostic assays from a single input sample and does so in fashion that overcomes the aforementioned limitations.

In one aspect, there is a cartridge that consists of a fluidic assembly that is made up of a top part, a spacer, and a bottom part all bonded together. The top part and bottom part have a plurality of fluidic channels. The top part may have a sample entry point that is used to fill a sample chamber, a detection channel where the diagnostic assay takes place, at least one blister peck for on-board liquid storage, a reagent channel, a waste compartment, a bubble minimizing compartment, and/or inlet holes to facilitate air or liquid movement within said channels. The bottom part may contain various fluidic channels that link features on the top part. The spacer may provide a plurality of capillary stops and/or holes to connect bottom part channels to top part channels. In particular, the cartridge may provide for opposing fluid delivery pathways for the sample versus other assay reagents in terms of their arrival to the detection channel. By this means, there can be prevention of sample leaking back into the detection zone of the detection channel during subsequent assay steps. Key to this arrangement is the position of the sample chamber relative to the sensor region, providing that the entry point hole(s) for reagents into the detection channel is not in a pathway that can be touched by the sample fluid. All reagents and mechanisms can be self-contained, thereby providing no evident means for outside tampering, and thereby ensuring reliability and reproducibility of test results.

In another aspect of the invention, there is provided a method for conducting a diagnostic assay. A biological sample is obtained from a patient. Then the sample chamber of the cartridge is filed with said sample. The cartridge is docked into a reader module that is capable of electromechanical functions. Through the application of pressure via pumps with venting valves to inlets on the cartridge assembly, the reader can push sample to the detection channel, oscillate said sample as to agitate any present assay chemistries, then mechanically and controllably burst a liquid-containing blister peck to fill a reagent channel, alternately push air and reagent liquid through the detection channel as to wash and/or initiate a detection reaction, and take measurements by interrogating the detection channel and store test data. Additionally or alternatively, the method may include actions that pull rather than push liquids to certain locations. The operating procedures would be characterized by all combinations of pulling or pushing actions. The method of the diagnostic assay is fully automated for the exception of the sample loading step. Therefore, the process saves time and effort on the part of the user and the precise liquid and air control provides greater accuracy and precision.

In an embodiment of the invention, the detection method for conducting an assay may be selected from a group including but not limited to absorbance, chemiluminescence, fluorescence, and/or magnetic, but most preferably an electrochemical means. Therefore, the cartridge can be tailored to a detection mechanism that maximizes performance for a given assay.

In a further embodiment of the invention, the cartridge can perform different assays from a group that includes but is not limited to immunoassays, molecular assays, electrolytes, chemistries, coagulation and/or hematology. The flexibility of the platform permits testing of various bio-markers across assay type. For a given patient, several markers of different types may need to be interrogated to provide critical information for the physician.

In yet another embodiment of the invention, the electrochemical detection method relies on a plurality of screen printed sensors. An array may be made from a multi-step process of screen printing inks and drying them onto a flexible substrate. Additionally or alternatively, an array may be made by directly printing inks on the bottom part The sensor array may consist of, for example five electrodes: a reference electrode, two control electrodes, a working sensor electrode, and a conductimetric electrode. The presence of on-board test control electrodes improves the function of calibration. With negative and/or positive controls, the test cartridge would suffer less from time dependent inaccuracies related to factory-based lot-to-lot calibration. The conductimetric electrode provides a means for detecting presence of liquid and the ability to measure its conductivity that allows calculation of hemetocrit when the sample is blood. This value can lead to a more accurately calculated analyte concentration. Alternatively, the array of five electrodes may be: a reference electrode, three working sensor electrodes, and a conductimetric electrode. The ability to do diagnostic panels via the multiple sensor electrodes, where two or more distinct tests are within the channel, is greatly appreciated in the medical community as there may be several biological indicators that contribute to a diagnosis.

In another embodiment of the invention, the cartridge contains a minimum of one blister peck capable of storing necessary liquids for diagnostic assays. The contents may consist of substrate reagent, washing solutions, buffer solutions and/or combinations thereof (collectively or individually "assay fluids"). The blister pack may be cylindrical in shape and may contain a deformable top layer that provides a cavity for liquid storage and a bottom layer that seals the liquid in. The bottom layer of the pack can be ruptured given the appropriate mechanical pressure from above and contact with a sharp feature that sits underneath. The blister provides hermetic storage and physical protection of the liquid components, minimizing degradation of the reagents, which can take place.

In another embodiment, the reader module may contain at least one mechanical actuator to compress a blister pack at least to the point of rupture, thereby releasing its contents to a reagent storage channel.

In another embodiment, the reader module may contain an actuator coupled to a diaphragm that provides controlled pressure to the air inlets by pressing and depressing a diaphragm bladder on the cartridge.

In another embodiment of the invention, the sample chamber is designed with particular dimensions and shape to control the volume that is being inputted to a certain measurable amount. This aspect permits the user to input an unmeasured volume rather than pre-measuring a specific amount. The user can be relieved of such a task and the cartridge can accurately dispense the desired amount for a given assay procedure.

In yet another embodiment, the sample chamber contains a means to separate plasma from other blood components before entering the detection channel, wherein the diagnostic assay is conducted on the plasma. The sample chamber may contain a filter to separate red blood cells and extract plasma through a time dependent wicking effect or the sample can be pushed through said filter with external pressure. Alternatively, there may be a second distinct part of the sample chamber that holds the resulting filtered sample before its release to the detection channel. The non-plasma blood components convolute the measurement accuracy of the analyte concentration. By removing such species, the test may encounter reduced signal interference from said constituents.

In yet another embodiment, the cartridge may contain one way valves as to prevent back flow of various liquids that could disrupt assay performance. These valves would be present between the sample chamber and the detection channel; between the detection channel and reagent storage channel; and/or in an embodiment with two blisters, between the substrate blister pack with direct connection to the detection channel and the channel itself.

In a specific embodiment, the electrochemical immunoassay, the cartridge contains screen printed sensors and other regions that are modified with antibody conjugates and certain liquid storage. Specifically, each working sensor electrode is amended with capture antibodies targeting a particular analyte and/or they are modified to serve as positive or negative sensor controls. Reporter antibodies, antibodies amended with enzymes, are dried and/or stabilized either within: an external sample transfer device, the sample chamber(s), channel that connects sample chamber to detection channel and/or within the detection channel region in proximity to the sensors or on the sensor strip itself. There may be two blister packs, one containing a wash solution and the other containing an electrochemical substrate. During operation, a user submits a biological sample to the sample chamber of cartridge and inserts said cartridge into a reader module. The sample is infiltrated with reporter antibodies and allowed to form antibody "sandwich" with the analyte(s) and the capture antibodies in the detection channel. After sandwich formation, the sensor region is evacuated of sample with air and liquid wash segments. A substrate fluid is passed over the sensor region and an electrochemical measurement is recorded. The user then may take the cartridge out of the reader and dispose of it. In this cartridge format, the user has a means for conducting lab quality assays that provide high performance, rapid assay time, and attractive economics due to the simplicity, reliability, and reproducibility of the cartridge construction and method of operation.

In certain embodiments of the present invention, a cartridge for sensing at least one analyte comprises a detection channel having a first end and second end; at least one analyte sensor, wherein said analyte sensor comprises at least one sensor electrode and said sensor electrode is within said detection channel between the first end and the second end; a reagent channel, said reagent channel connected to said detection channel between the sensor electrode and the second end; a sample chamber, said sample chamber connected to said detection channel between the sensor electrode and the first end; and a waste compartment connected to said detection channel at the first end.

In certain embodiments of the present invention, the cartridge further comprises a first inlet connected to the sample chamber, wherein pressure applied to said first inlet moves a sample contained in the sample chamber from the sample chamber to the detection channel.

In certain embodiments of the present invention, the cartridge further comprises a second inlet connected to the detection channel at the second end, wherein pressure applied to said second inlet pushes at least one of the sample and an assay fluid from the detection channel to the waste compartment.

In certain embodiments of the present invention, the sample or the assay fluid pushed from the detection channel to the waste compartment is substantially prevented from leaking back into the detection channel.

In certain embodiments of the present invention, the cartridge further comprises at least one blister pack for on-board liquid storage; and a bubble trap connecting the blister pack to the reagent channel, wherein a liquid stored in the blister pack moves from the blister pack to the reagent channel through the bubble trap, and wherein the bubble trap traps air bubbles when the liquid moves through the bubble trap.

In certain embodiments of the present invention, the assay fluid is at least one of a substrate reagent, a washing solution and a buffer solution.

In certain embodiments of the present invention, the blister pack is not vacuum filed.

In certain embodiments of the present invention, the analyte sensor comprises an array of electrodes. The electrodes may comprise at least two of a reference electrode, a working sensor electrode and a conductimetric electrode. The electrodes may comprise at least three of a reference electrode, a working sensor electrode, a counter electrode and a conductimetric electrode.

In certain embodiments of the present invention, a cartridge for sensing at least one analyte comprises a detection channel having a first end and second end; at least one analyte sensor, wherein said analyte sensor comprises at least one sensor electrode and said sensor electrode is within said detection channel between the first end and the second end; a reagent channel, said reagent channel connected to said detection channel between the sensor electrode and the second end; a sample chamber, said sample chamber connected to said detection channel between the sensor electrode and the first end; a waste compartment connected to said detection channel at the first end; and an inlet connected to the detection channel at the second end, wherein pressure applied to said inlet pushes at least one of a sample and an assay fluid from the detection channel into the waste compartment.

In certain embodiments of the present invention, pressure applied to the inlet may be positive pressure or negative pressure.

In certain embodiments of the present invention, pressure applied to the inlet may be used to oscillate the assay fluid.

In certain embodiments of the present invention, the analyte sensor comprises at least three of a reference electrode, a working sensor electrode, a counter electrode and a conductimetric electrode.

In certain embodiments of the present invention, the cartridge further comprises at least one blister peck for on-board liquid storage; and a bubble trap connected to the blister pack and to the reagent channel, wherein the bubble trap traps air bubbles within assay fluid transferred from the blister pack through the bubble trap to the reagent channel.

In certain embodiments of the present invention, a method for performing a diagnostic assay on a cartridge comprises inputting a sample into a sample chamber; applying pressure to a first inlet to move the sample from the sample chamber to a detection channel connected to the sample chamber, wherein the detection channel has a first end, a second end, and at least one sensor electrode between the first end and the second end, and wherein the sample chamber is connected to the detection channel between the sensor electrode and the first end; applying pressure to a second inlet to transfer the sample from the detection channel to a waste compartment connected to the detection channel at the first end, wherein the second inlet is connected to the detection channel at the second end; and applying pressure to a third inlet to transfer reagent liquid from a reagent channel to the detection channel, wherein the reagent channel is connected to the detection channel between the sensor electrode and the second end.

In certain embodiments of the present invention, the method further comprises applying pressure to a blister peck to transfer assay fluid to the reagent channel; and trapping air bubbles from the assay fluid in a bubble trap connecting the blister pack to the reagent channel.

In certain embodiments of the present invention, the method further comprises oscillating the assay fluid in the detection channel by applying pressure to at least one of the first inlet, the second inlet and the third inlet.

In certain embodiments of the present invention, the sample transferred to the waste compartment is substantially prevented from leaking back into the detection channel.

In certain embodiments of the present invention, the method further comprises contacting the sample with at least two of a reference electrode, a working sensor electrode and a conductimetric electrode in the detection channel.

Other features and advantages of the invention will be apparent from the accompanying drawings and from the detailed description. One or more of the above-disclosed embodiments, in addition to certain alternatives, are provided in further detail below with reference to the attached figures. The invention is not limited to any particular embodiment disclosed; the present invention may be employed in not only sensor applications, but in other applications as well.

BRIEF DESCRIPTION OF THE DRAWINGS

The invention is better understood from reading the following detailed description of the preferred embodiments, with reference to the accompanying figures in which.

Features, elements, and aspects of the invention that are referenced by the same numerals in different figures represent the same, equivalent, or similar features, elements, or aspects in accordance with one or more embodiments of the system. Those of ordinary skill in the art will appreciate that features, elements and aspects of the invention depicted in the figures in a similar or Identical manner may be similar or identical, even if, for example, a plurality of such features, elements and aspects are not individually labeled.

DETAILED DESCRIPTION

Figure 1:
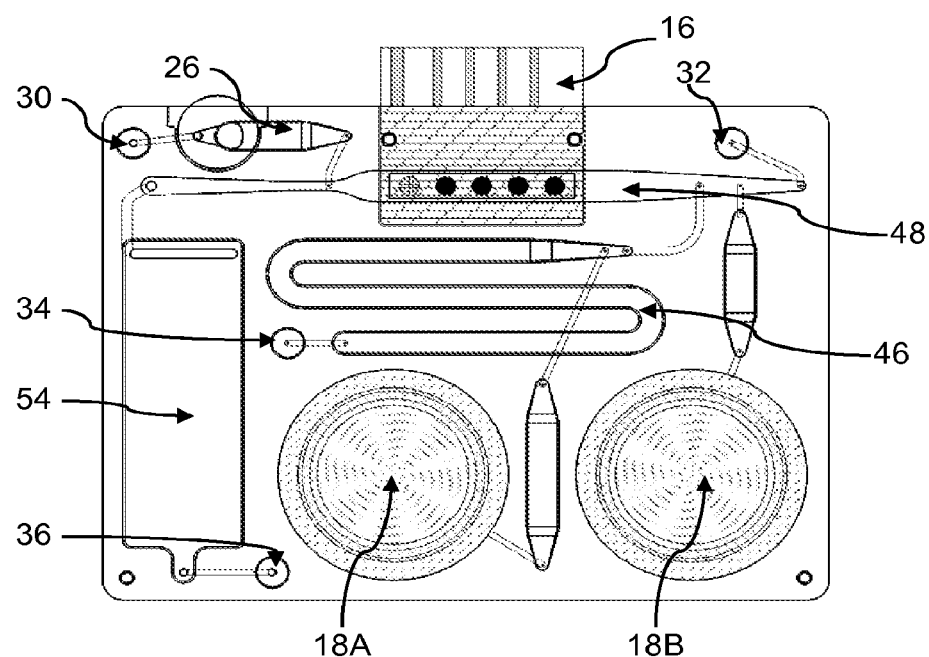
FIG. 1 is a schematic diagram depicting the top view of a fully assembled cartridge with dual blister packs.

A description of the present invention along with detail for methods of operation and an example of its use is provided. The invention primarily comprises a cartridge for conducting diagnostic assays. Referring to FIG. 1, a cartridge consists of several components assembled together with on-board liquid storage in the form of two blister packs. One blister pack may contain washing fluid and another may contain substrate reagents. Alternatively, referring to FIG. 2, a cartridge can consist of those same components but with a single blister pack for on-board liquid storage. For this configuration, the substrate solution also serves as a washing agent. For the purposes of description, herein we will detail the dual blister pack cartridge.

Cartridge Assembly and Components

Figure 3:
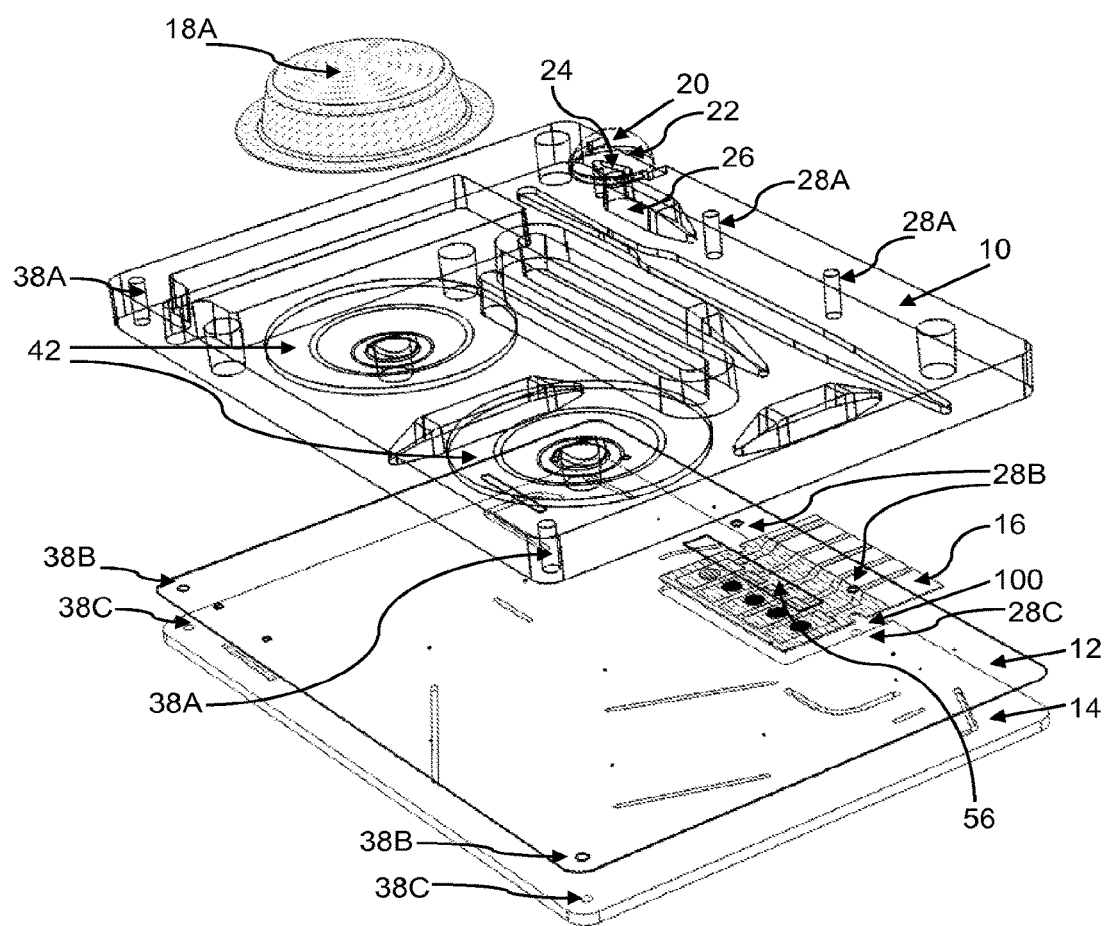
FIG. 3 is an exploded view of the cartridge showing the major components: blister pack, top pert, spacer, sensor array, bottom part.

Referring to FIG. 1, in accordance with an experimental embodiment of the present invention, the fully assembled dual blister pack cartridge can be constructed as follows. Referring to FIG. 3, a sensor array 16 is placed in the inset 100 of a bottom part 14 and lined up in a rig using alignment holes 28C. This substructure is combined and secured with a thin film spacer 12 that can be bonded or adhered to the bottom part using alignment holes 28B, 28C, 38B and 38C. The spacer contains a cut-out 56 to leave the sensor array exposed. Next, a top part 10 can be bonded and/or adhered to the top side of the spacer 12 using alignment holes 28A,B and 38A,B. Blister packs 18A and 18B containing sealed liquid may be affixed to a recess 42 in the top part by a ring shape adhesive film (not shown). A sample lid 20, may be placed over the sample recess 22 to seal the sample chamber 26.

Referring to FIG. 3, the blister pack 18A,B consists of a flat-top cylindrical shape that may be made from a cold formable material whereby a molded, defined shape is pressed upon the cold formable film as to take on the design of the mold. The cold formable material may be an aluminum foil that is laminated on either side by a thin polymeric film. The cavity that results is filed with liquid reagent solutions needed for conducting an assay. In the description, blister 18A contains a wash solution and blister 18B contains a substrate solution. The cavity can provide 50 uL to 3 mL of volume and the blister can be under-filled or altered in its dimensions as to adjust the volume capacity. Blister 18A is filled to less or equal the volume of the reagent channel 46. Blister 18B is filled to excess of the volume of the detection channel. Once the cavity is filed, it can be hermetically sealed with by placing a thin layer of material on top of the cavity and applying pressure and/or heat. The sealing material may an aluminum film whereby the sealed side is coated with a glue-like lacquer that activates upon pressure and/or heat. The other side may have a protective lacquer that is not disrupted by heat. The use of aluminum provides ultra low vapor transmission so that no liquid escapes or enters once sealed.

Referring to FIG. 4A-D, an electrochemical sensor array 16 can be fabricated for use as the means of detection for the cartridge. The following refers to an array containing five electrodes but the arrangement may be altered to increase or decrease the number of electrodes, as well as to alter the composition and type of electrodes. For example, instead of using only one reference electrode as a mean to set solution potential, a pair of counter and reference electrodes can be used for more accurate liquid potential control. Those of ordinary skill in the art will appreciate the different formats for various electrode arrangements.

Figure 4A:
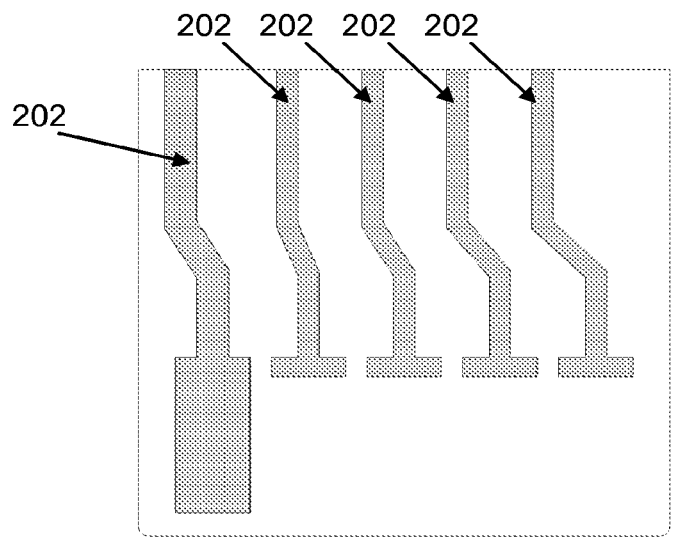
FIG. 4A-D is schematic of a screen printed electrode sensor array and its fabrication process.

Referring to FIG. 4A, the sensor array may be fabricated by first screen-printing silver ink contact traces 202 on a plastic flexible substrate 200 and/or directly onto the bottom part 14.

Figure 4B:
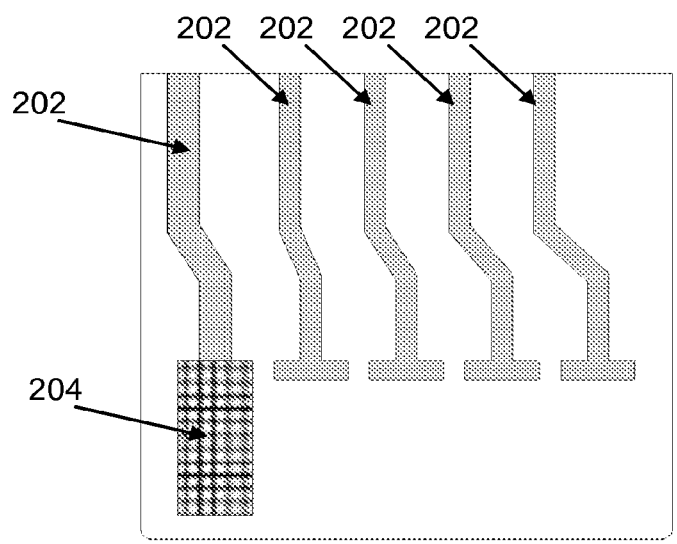

Referring to FIG. 4B, silver/silver chloride (Ag/AgCl) inks may then be screen-printed to form a reference electrode 204.

Figure 4C:
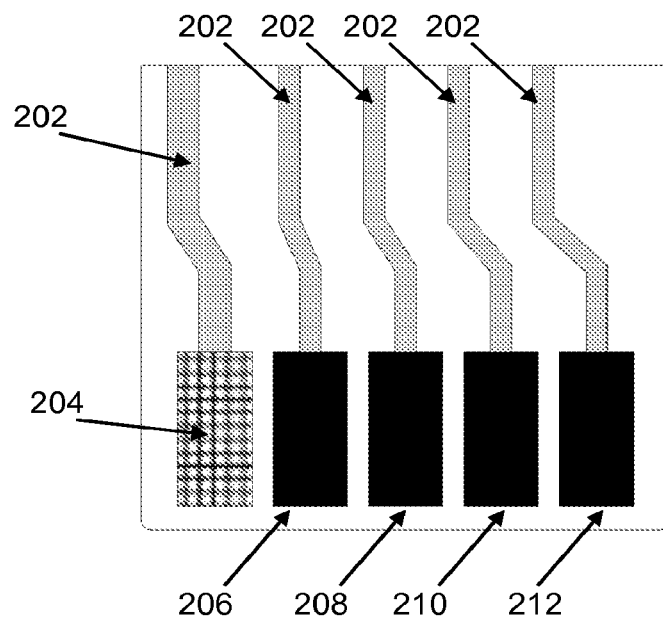

Referring to FIG. 4C, carbon inks (e.g., proprietary inks) may then be screen-printed to form four electrodes 206, 208, 210, 212 that may be used as working electrodes, sensor electrodes, or conductimetric electrodes.

Figure 4D:
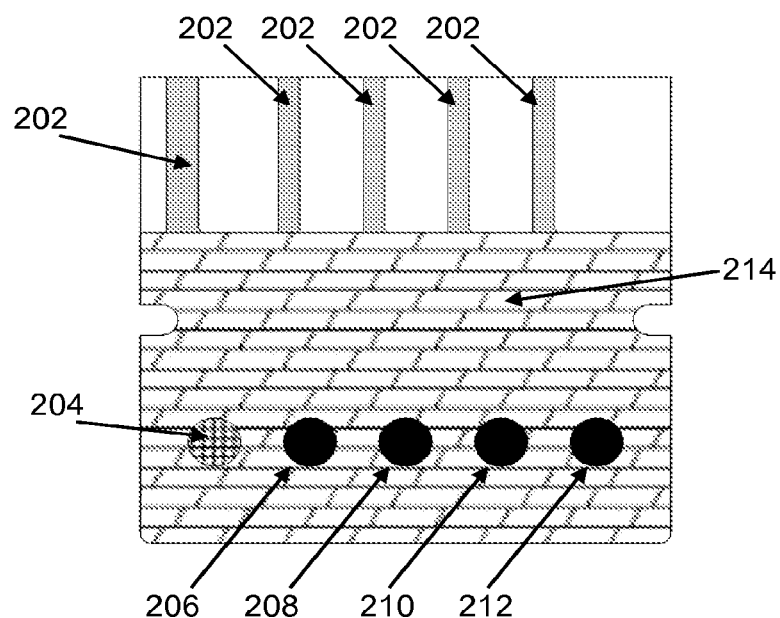

Referring to FIG. 4D, a dielectric insulation layer 214 may then be screen-printed, for example, to cover portions of the silver traces and expose certain regions of the carbon electrodes and reference electrode. This coverage permits the array to be exposed to liquid immersions as when conducting a diagnostic assay. The result is a printed sheet containing a plurality of electrodes that may be utilized for electrochemical sensing.

For example, in an electrochemical immunoassay, electrodes 208, 210, 212 may be used respectively as positive control, negative control, and sensor. Electrode 206 would act as conductimetric sensor. Biological molecules are coated onto such electrodes in a controllable fashion by a liquid dispenser. For the positive control, a known quantity of target analyte, or reporter antibody, or anti-reporter antibody that captures constituents of reporter antibodies is affixed and saturated to the surface. For the negative control, antibodies that are not specific to the analyte or other inert moieties are affixed to the surface as to prevent any target analyte binding. Finally, the capture antibodies specific to the target analyst are affixed to the sensor electrode surface. Corresponding reporter antibodies would be introduced in another part of the cartridge.

Alternatively, the array can be used for simultaneously conducting multiple assays. In this arrangement, two or more of the electrodes 206, 208, 210, 212 would each be modified with capture antibodies for a specific analyte. Electrodes not modified as sensors may be modified as negative or positive controls. Corresponding reporter antibodies to the specific analytes would be introduced in another pert of the cartridge.

This inclusion of test control electrodes provides on-board calibration by normalizing the signal from controls to the active sensor's signal. Otherwise, shelf-life dependent calibration codes would have to be implemented on the cartridge. For example, such calibration codes may be printed directly on a label or as a bar code on a label that is stuck on the cartridge.

Figure 5:
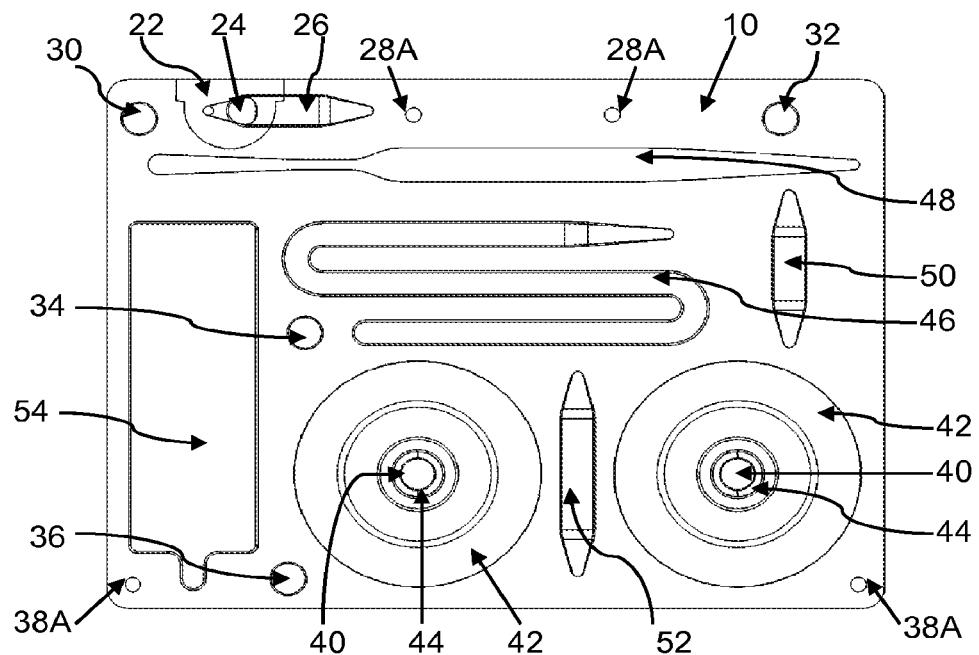
FIG. 5 is a schematic diagram of the top view of the top part for the cartridge.

Referring to FIG. 5, top part 10 contains many features for conducting a diagnostic assay. These features are produced by injection molding of plastic to form channels, contours, holes, and other 3D shapes. The channel surfaces may include irregularities (e.g., structural), for example within the reagent channel 46, in order to facilitate mixing. For the purposes of diagnostic assays, the plastic chosen should be compatible with biological molecules and detection chemistries and have good moisture barrier properties. The plastic may be chosen from a group including but not limited to polystyrene, polycarbonate, and/or polypropylene. The plastic may be coated with chemistries or exposed to plasma in order to make it hydrophobic or hydrophilic in certain regions. The sample chamber 26, channel 104, sensor strip 16 and detection channel 48 may have assay conjugates dried in their regions. Additionally, the conjugates may be amended by stabilizer. For example, an assay conjugate for an electrochemical immunoassay would be reporter antibodies, antibodies amended with an enzyme that produces an electroactive product. The reagent channel 46 and/or channel 112 may have dried chemical species (e.g., substrate)

that mix with liquid upon its introduction from the blister pack 18A due to the nature of the channel.

Figure 6:
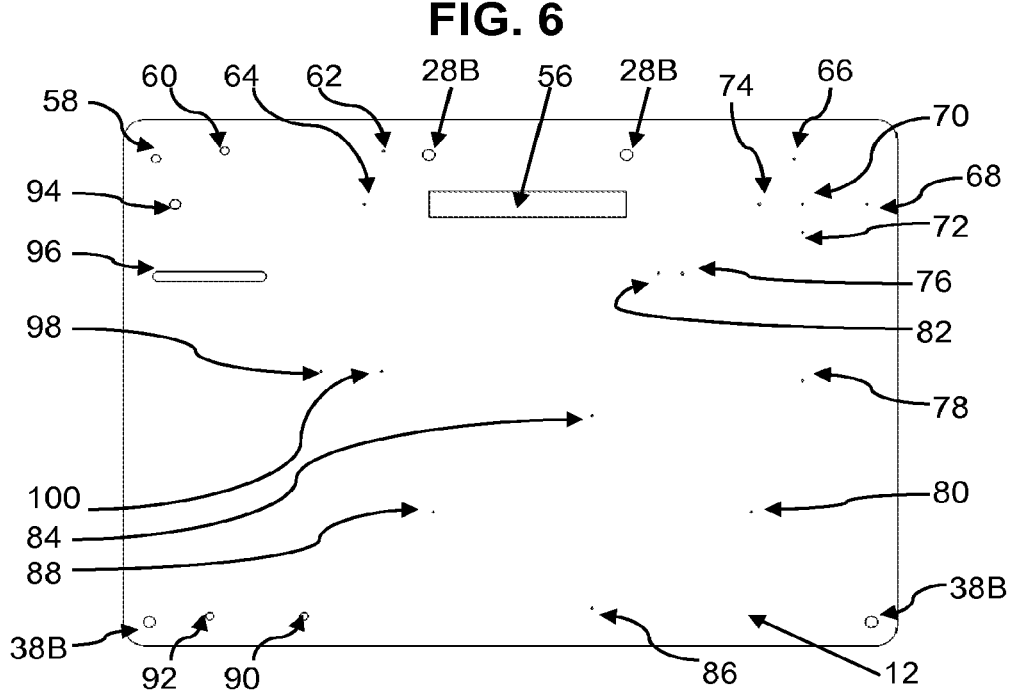
FIG. 6 is a schematic diagram of the top view of the spacer for the cartridge.

Referring to FIG. 6, the spacer 12 contains several cut-outs and holes. The material may be a flexible plastic film that is coated on both sides by pressure sensitive adhesive, thereby providing a sealing function. The cut-out and holes can be made by laser cutting. The holes may act as capillary stops to provide resistance to liquid flow until a certain pressure is applied. The dimensions of the holes may be tailored to specify these effects.

Figure 7:
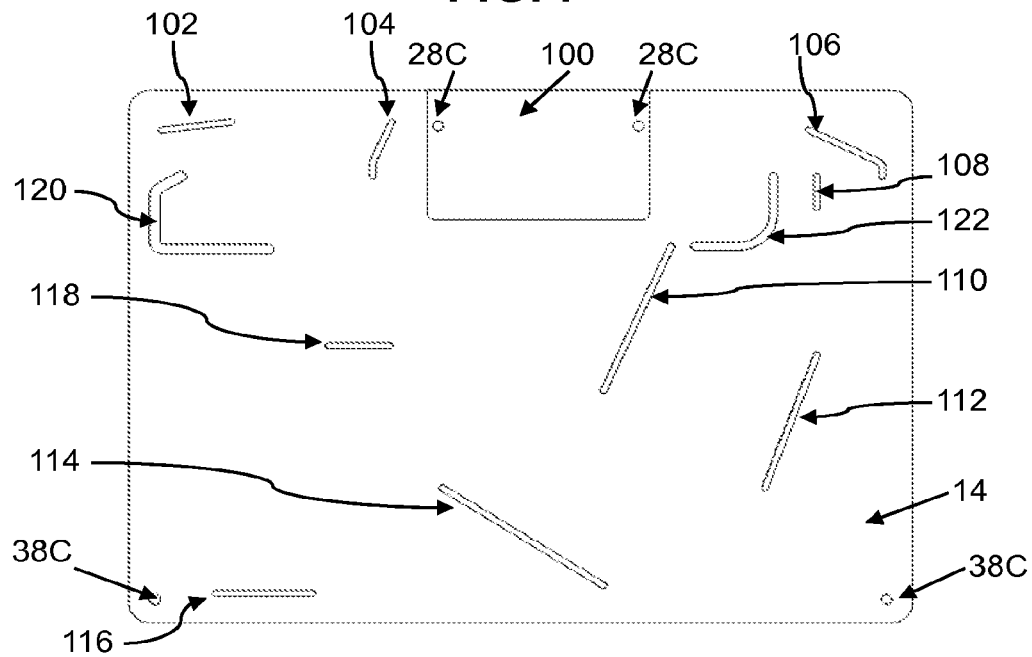
FIG. 7 is a schematic diagram of the top view of the bottom part for the cartridge.

Referring to FIG. 7, the bottom part 14 contains various fluidic channels and can be made from, for example, various plastics similar to the top pert 10. In any case, the material may be fairly flexible to ensure an appropriate seal when combined with the other components.

Referring to FIGS. 1-7, there are features present that can contribute to fluid control and manipulation by way of combining elements within the top part, spacer, and/or bottom part. Generally, this is performed by external pumps with vents that access inlets 30, 32, 34, and 36, use paths governed by holes acting as capillary stops in the spacer combined with channels contained within the top part and bottom pert. Alternatively, the application of pressure at the Inlets may be done by an external diaphragm displaced by an actuator. Alternatively, one-way valves may be introduced in certain locations to prevent back flow contamination. The valves may be placed in channels 104, 108, and 122 of the bottom part.

The top part 10 contains a sample chamber 26 with sample inlet 24 that provides an opening for depositing a biological sample via a sample transfer device. A sample transfer device may include a volumetric pipette, a but pipette, a syringe or other device for holding and depositing fluid. A recess 22 is positioned around the perimeter of the Inlet 24 such that a lid 20 can be affixed on top as to close the sample chamber. The lid can be a removable plastic piece that can be coated with a weak adhesive. Additionally or alternatively, the lid can be incorporated within the top part during plastic molding in the format of a living hinge (not shown). A plastic ribbon would connect top part to the lid and a user may fold over the ribbon to cover or plug the sample inlet 24 with the lid portion.

The sample chamber 26 is a domain that may be defined to be a particular volume ranging from 5-500 uL. The sample chamber may contain a filter in its bottom to extract plasma from an input sample of whole blood. The filtration may act by wicking the blood over time or the liquid is forced through the filter by external pressure.

To move sample from the chamber to the detection channel, pressure can be applied by an external pump to inlet 30, which follows the path from holes 58, 60 via channel 102. The liquid then travel from holes 62, 64 via channel 104 and enters the detection channel 48. In a possible method, the sample is detected by a conductimetric electrode at position 206 and the displacement is stopped with the sample fully covering the sensor array 16.

From inlet 32, the sample in the detection channel 48 can be oscillated by applying pressure from holes 66, 68 via channel 106. The oscillation can be performed by an external pump and can displace air at varying frequencies for a specified duration. Additionally, pressure through inlet 32 from holes 66, 68 via channel 106 can force sample from the detection channel 48 to the waste compartment 54 from hole 94 to cutout 96 via channel 120. For this defined pathway, air segments of known volume may also be generated and pass through after liquid has been removed. Alternatively, a dedicated air inlet may be introduced next to inlet 32 (not shown) that would serve the air oscillator function exclusively. In this manner, the dead volume from a shared inlet would be minimized.

For blister packs 18A, 18B, an external mechanical actuator applies downward pressure to the top of the individual pecks until compressed. For example, this may be a pneumatic or hydraulic piston. The blisters sit in recess 42 and a sharp molded feature 44 punctures the bottom of the blister upon this external pressure. The liquid from the blister is then forced through an opening 40.

For blister pack 18A, the wash liquid that enters opening 40 may be moved from holes 88, 86 through channel 114 arriving at bubble trap 52 and then continue from hole 84, 82 via channel 110 and fills the reagent channel 46. The bubble trap is an oblong domain that is meant to trap any air bubbles that form within the liquid released from said blister from either dead volume within the blister or bubbles generated from piercing of the bottom blister layer. The trap can minimize bubbles from entering the detection region and prevent fouling of the assay process. Inclusion of the bubble trap can obviate the need to vacuum fill the blister(s).

During compression of blister pack 18B, the substrate liquid is moved from holes 80, 78 through channel 112 to enter bubble trap 50 and continues flowing by exiting from hole 72, 70 via channel 108 and fills the detection channel 48.

Figure 2:
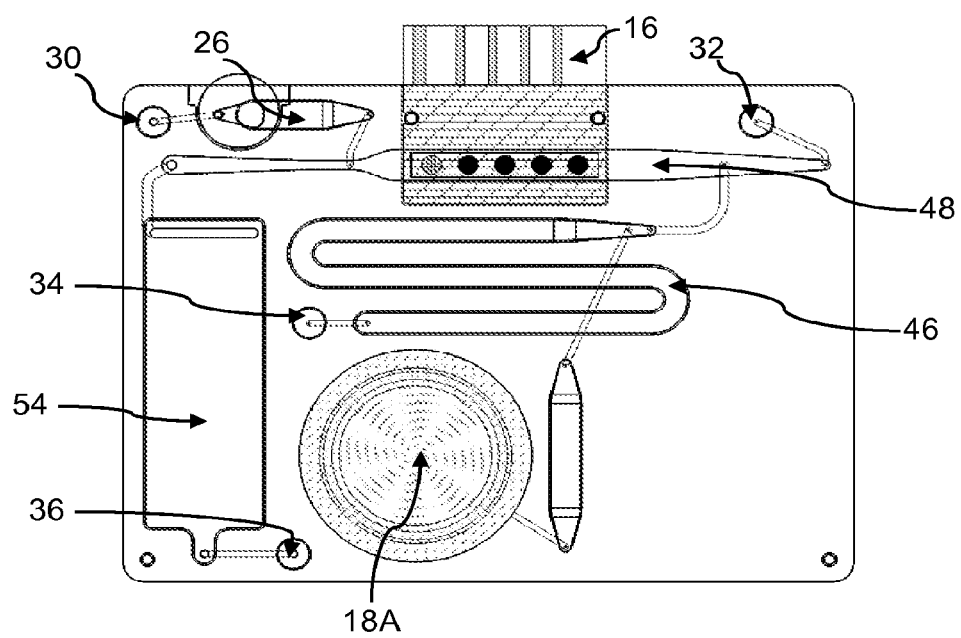
FIG. 2 is a schematic diagram depicting the top view of a fully assembled cartridge with a single blister pack.

Referring to FIG. 2, a cartridge with a single blister pack would follow the same path for blister pack 18A. In this configuration, the wash and substrate solution are stored as one mixed liquid and released from the blister into the reagent channel.

Regardless of dual or single blister packs, once the reagent channel 46 is filled, this fluid can be pushed in controlled segment volumes, that is, a portion of the total volume in the reagent channel is released at a given flow rate and the process repeated. The force is provided by applying pressure to inlet 34 from holes 98, 100 via channel 118. The liquid residing in the reagent channel moves from holes 76, 74 through channel 122 to get to the detection channel 48. The liquid that is passed over this area may be used to periodically wash the sensor array and/or introduce substrate reactant to yield an electroactive product for detection. Ultimately, all liquid ends up in the waste compartment 54 through the channel pathway that was stated for the sample flush.

The waste compartment 54 is a domain that can hold, for example, 100-6000 uL of liquid. The compartment contains an absorbent pad (not shown) that is cut to match the dimensions of the compartment. The pad soaks up the different assay liquid components and substantially prevents the fluids from leaking back into the detection channel. Absorbent materials such as cellulose fibers, hydrophilic-modified olefin fibers, and/or super absorbent polymers may be used to form such pad. Air inlet 36 has access to the waste compartment via channel 116 through holes 90, 92. The purpose of this inlet is to permit venting of the compartment during certain operations. An external valve can administer this action by connection to inlet 36. In other operating modes, this inlet can be used to apply negative pressure, so fluid is pulled from the detection channel 48 to the waste compartment 54.

Operation Modes of the Cartridge

Figure 8:
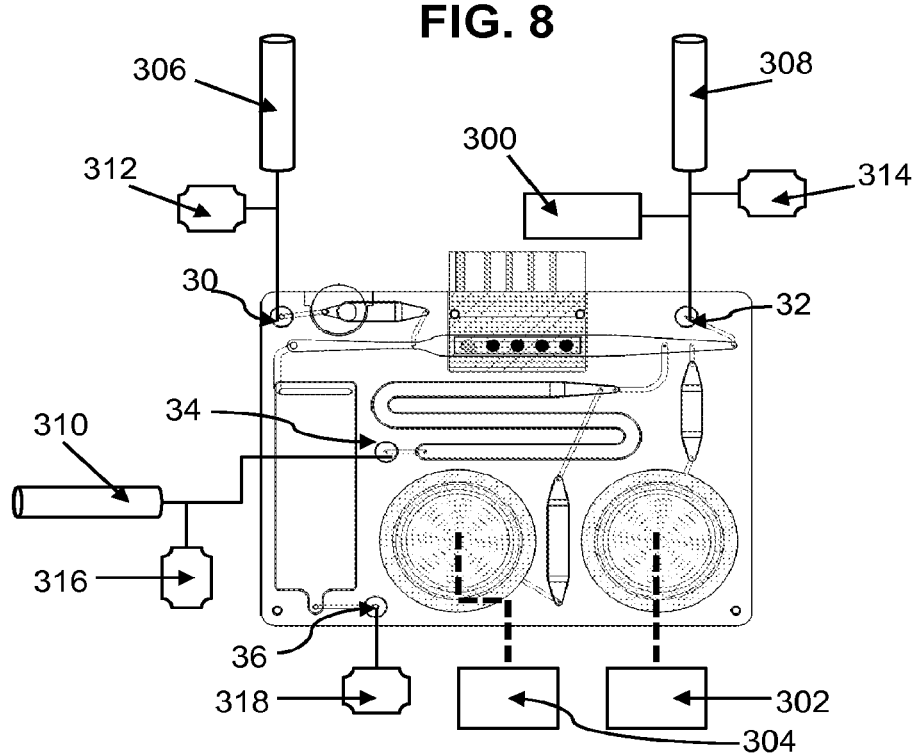
FIG. 8 is a functional diagram of electro-mechanical elements engaged with the cartridge.

Generally, for a mode of operation, the cartridge is manipulated by a corresponding reader module. Referring to FIG. 8, the reader according to an embodiment of the present invention contains vent valves 312, 314, 316, and 318 and/or pumps 306, 308, and 310 that access the cartridge through inlets 30, 32, 34, 36. Herein the valve or pump that addresses a particular inlet will be denoted. The open/close valves may be of pinch or diaphragm types or other variety. The pump may be a syringe pump, solenoid pump, diaphragm pump, piezoelectric pump or other variety.

At the onset, all four valves 312, 314, 316 and 318 are opened. The sample pump 306 has approximately 1 mL of air. The air pump 308 and the reagent pump 310 each have approximately 3 mL of air.

A cartridge is loaded with sample and engaged with the reader. The loaded sample may be of volume 50-500 uL (preferably 30-100 uL). There is an initial setup routine to make sure that the cartridge aligns with fixtures and that the cartridge's contact pads are registered with an electrical connector. The pumps 306, 308, and 310 are connected to their corresponding inlets with tubing with inner diameter 1/32"-1/16" and a fitting compliant with the Inlet opening. The tubing may be flexible plastic or rubber.

For sample movement from the sample chamber 26 to the detection channel 48, valve 314 is opened and valves 312, 316, and 318 are closed. Pump 306 pushes air at a rate of 1-100 uL/s and that drives the sample. Simultaneously, the electrical conductivity between reference electrode 204 and conductimetric electrode 206 is recorded. When conductivity is measured over a particular threshold value, pump 306 pushes an additional volume of 0-50 uL, preferably 20 uL until stopping. If the sample is blood, then a calculation of hematocrit is made from the conductivity measurement.

In the next step, valves 312, 314, 316, and 318 are closed or alternatively valve 318 is opened and valves 312, 314, and 316 are closed. An air oscillator 300, a separate pump that is capable of displacing air in the range of 1-200 uL, preferably 25-50 uL, is switched on for 2-30 minutes or preferably 8-12 minutes. The oscillator has access to inlet 32 but is not managed by valve 314. The frequency range is 0.1-1000 Hz, preferably 2-20 Hz. Diaphragm or piezoelectric pumps can be used for oscillation. The oscillation facilitates the assay chemistry. After the oscillations are completed, valve 318 is opened and valves 312, 314, and 316 are closed. Then pump 308 introduces 300 uL of air at a rate of 100 uL/s. By doing so, nearly the entire sample is sent to waste compartment 54.

After this, valve 316 is opened and valves 312, 314, and 318 are closed. An actuator 304, either a hydraulic or pneumatic piston compresses blister pack 18A and fills the reagent channel 46. The compression may be controlled by monitoring the pressure reached in the hydraulic or pneumatic system.

For the washing procedure, valves 312, 314, and 316 are closed and valve 318 is opened. Pump 310 introduces 100-1000 uL of air at rate of 50-500, uL/s, preferably 500 uL at 300 uL/s. As a result, a portion of the liquid in the reagent channel 46 is delivered to the detection channel 48. Then after waiting 0-10 seconds, preferably 5 seconds, pump 308 introduces 10-500 uL of air at a rate of 5-500 uL/s, or preferably 200 uL at 25 uL/s. This flushes the reagent out of the detection channel 48 to the waste compartment 54. These steps are then repeated 2-10 times, preferably 5 times, in order to introduce alternating liquid and air segments to the detection channel.

The measurement is done by first compressing the blister pack 18B by an actuator 302 similar to the one that addresses blister pack 18A. The substrate fluid fills the detection channel 48. The reader records the electrochemical signal, for example amperometrically, for a predetermined time 1-100 seconds, preferably 30 seconds. Using an internal algorithm, the signal is processed to report an analyte concentration.

After the measurement, all valves are opened, the actuators are withdrawn and all pumps are reset to the start configuration. The cartridge now can be removed from the reader and discarded. The total operation time per assay (assay turnaround time) can be less than 15 minutes.

Alternatively, the operation described can be used for a single blister pack cartridge as in FIG. 2 with limited alteration to the protocol. In this case, the content of the blister is a combined wash/substrate solution. For this procedure, the blister 18A is applied for both the washing procedure and measurement steps according to nearly the same parameters specified for the dual reagent cartridge. This blister's solution fills the reagent channel 46 and is addressed by valve 316 and pump 310. Therefore, during the washing step where liquid and air segment are alternated in the detection channel 48, there is now a final liquid introduction where the solution is kept in the detection channel. At this point, the solution is allowed to initiate the electrochemical reaction and a measurement is carried out similar to the dual reagent procedure.

The aforementioned operation modes are characterized by a so-called "push" format because of positive air pressure that is used to "push" actions to the inlets. Alternatively, the procedure may apply negative air pressure and "pull" fluid through the same mechanisms of pumps and valves. Those of ordinary skill in the art will appreciate the different formats for conducting additional yet functionally equivalent procedures that employ combinations of pulling or pushing through the cartridge inlets.

Example of Diagnostic Assay—Troponin I

Troponin I is a specific marker for the degradation of heart tissue. Therefore, quantitative measurement of cardiac Troponin I is used to aid in the diagnosis of acute myocardial infarction (AMI) or heart attack. Because of the time sensitive and critical nature of AMI, it is important to have highly accurate and precise readings, especially for ultra low concentrations of Troponin I, such as those less than 20 pg/mL. The following example is put forth so as to provide disclosure of how to construct and use the diagnostic cartridge for an electrochemical immunoassay for the analyte, Troponin I. This example is intended as a nonlimiting example of the invention.

The sensor array 16 is prepared to provide conductivity sensor, positive control, troponin sensor, and negative control as 206, 208, 210, and 212, respectively. Blocking solution alone or blocking and nonspecific antibodies are deposited onto electrode 206. A saturated known quantity of reporter antibody, anti-troponin I amended with enzyme label, is deposited and affixed in place on electrode 208. Capture antibodies, anti-troponin I, is deposited onto electrode 210. Antibodies not specific to troponin I, anti-prostate specific antigen, is deposited into place on electrode 212. After each deposition, a solution that can contain bovine serum albumin (BSA), casein, fish serum, human serum, trehalose, sucrose and detergents like Tween20 may be applied to block any open attachment sites on the electrode surface.

An excess of assay conjugate, reporter antibody, can be deposited and dried in the sample chamber 26 and/or the detection channel 48. The reporter antibody is anti-troponin I amended with an enzyme. The deposited area may be further coated with saccharides like trehalose and sucrose or stabilizer solution to preserve the antibody integrity. Depending on the electrochemical scheme, the enzyme can be horse radish peroxidase (HRP), alkaline phosphatase (ALP), or others. For HRP, the corresponding substrates may be OPD, TMB, and ABTS. For ALP, the corresponding substrates may be PAPP, BCIP/NBT, and 1-Naphthyl phosphate. For example, an HRP enzyme with a TMB solution may be used.

The blister packs 18A, 18B are filled with a wash and substrate solution, respectively. The wash solution may be a PBS buffer solution with 0.05% Tween20 (PBST). The substrate solution may be TMB solvated in buffer solution.

To conduct an assay, a sample is deposited into the sample chamber and inserted into a reader module. The sample is moved to the detection channel. Next, the sample is oscillated within the chamber to reconstitute any dried reporter antibodies and accelerate antibody sandwich formation. Thereby, troponin binds to the capture antibodies and the reporter antibodies bind to the troponin. Once the sandwich complex is formed, the sample is evacuated to waste by an air segment. A small volume of wash solution is passed through the detection channel to remove unbound biological species such as reporters and other non-troponin sample constituents. Alternating air and wash liquid segments are employed to perform a rigorous wash and minimize non-specific binding. Finally, the substrate solution is released into the detection channel. The HRP enzyme of the reporter antibody reacts with TMB component in the substrate. The product of such an enzymatic reaction can be detected amperometrically or through other electrochemical methods by the electronic reader. The measured signal can be processed by the reader to output a troponin concentration reading.

Figure 9:
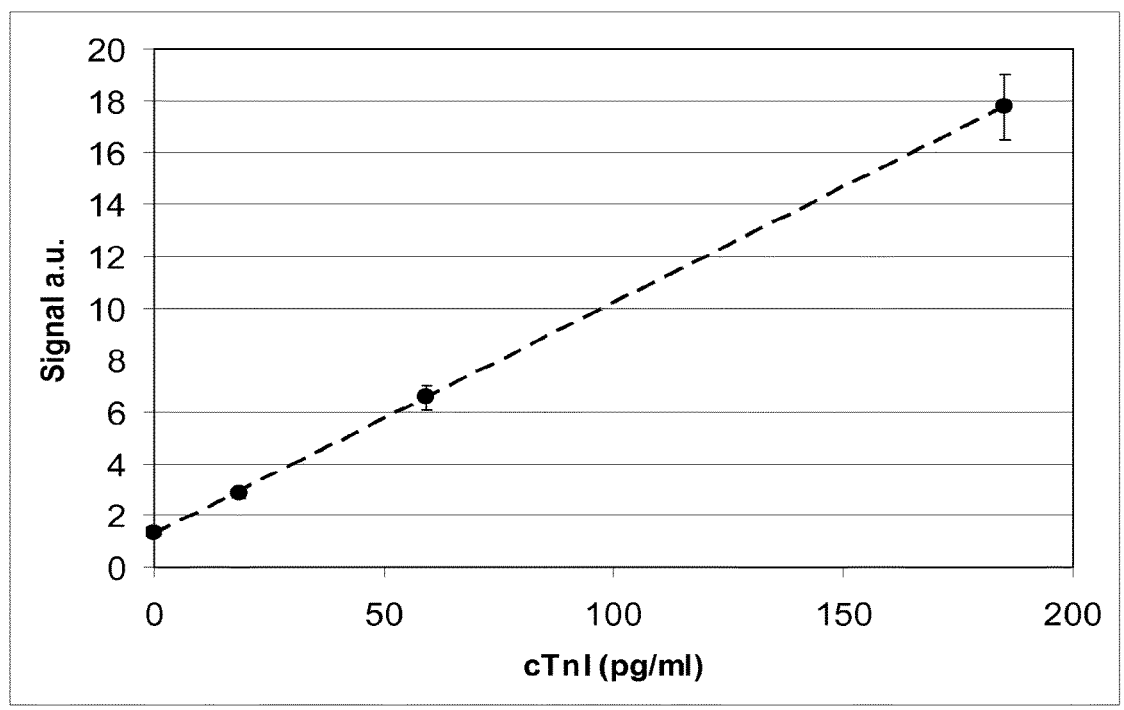
FIG. 9 is a data plot showing the response of the cartridge that performs an electrochemical immunoassay for Troponin I at various concentrations.

Referring to FIG. 9, such a cartridge can be prepared and tested with known concentrations of Troponin I in various sample matrices, whole blood, plasma, or buffer solution. The data plot shows the sensor response in whole blood and demonstrates the cartridge's ability to provide high performance over a low troponin concentration range. The concentration curve shows linear behavior and can be calibrated with such a function. One can calculate the limit of detection to be approximately 3 pg/mL using a standard procedure, thereby classifying the assay as ultrasensitive. In addition, the coefficient of variation (CV) for measurements of across low concentrations is approximately 7%. The CV is an indicator of precision and a value less than 20% at low concentrations indicates high capability for use in diagnosis of cardiac-related events.

What is claimed is:

1. A method of detecting a concentration of Troponin in a whole blood sample, the method comprising:
   inserting a diagnostic cartridge containing the whole blood sample in a sample chamber into a reader, the diagnostic cartridge having Troponin reporter antibody amended with an enzyme label in the sample chamber and/or in a detection channel; and
   operating the reader to
      move the sample out of the sample chamber into the detection channel and across an electrode array in the detection channel, a first electrode of the electrode array having affixed thereon an anti-Troponin capture antibody,
      move the sample out of the detection channel,
      move a wash liquid from a first reservoir in the cartridge into the detection channel,
      move the wash liquid out of the detection channel, and
      move a substrate solution out of a second reservoir into the detection channel, the substrate solution comprising a component reactive with the enzyme amended to the reporter antibody; and
      detect a reaction between the Troponin reporter antibody amended with enzyme and the substrate solution to measure the concentration of Troponin in the whole blood sample with a limit of detection of 3 pg/mL.

2. The method of claim 1 wherein the sample chamber has Troponin reporter antibody amended with the enzyme label deposited therein prior to the inserting step.

3. The method of claim 1 wherein the step of operating the reader to move the sample out of the sample chamber into the detection channel comprises operating the reader to move the sample into the detection channel from a first point of the detection channel on a first side of the electrodes, and wherein the step of operating the reader to move the substrate solution comprises operating the reader to move the substrate solution into the detection channel from a second point of the detection channel on a second side of the electrodes.

4. The method of claim 1 further comprising repeating the steps of operating the reader to move wash liquid into the detection channel and out of the detection channel prior to the step of operating the reader to move the substrate solution.

5. The method of claim 1 further comprising operating the reader to move air into the detection channel as the wash liquid is moved out of the detection channel.

6. The method of claim 1 further comprising operating the reader to move wash liquid out of the detection channel into a waste compartment in the cartridge.

7. The method of claim 1 wherein the step of operating the reader to move the wash liquid comprises operating the reader to move the wash liquid out of the first reservoir and into a reagent channel and from the reagent channel into the detection channel.

8. The method of claim 7 wherein a volume of wash liquid in the first reservoir is equal to or less than a volume of the reagent channel.

9. The method of claim 8 wherein the step of operating the reader to move the wash liquid comprises operating the reader to move a portion of the volume of wash liquid from the reagent channel into the detection channel.

10. The method of claim 1 wherein a volume of reagent in the second reservoir is greater than a volume of the detection channel.

11. The method of claim 1 wherein a second electrode of the electrode array has a Troponin capture antibody affixed thereon.

12. The method of claim 11 wherein a third electrode of the electrode array has an antibody not specific to Troponin affixed thereon.

13. The method of claim 1 wherein the detecting step comprises detecting amperometrically a reaction between the reporter antibody and the substrate solution to measure the concentration of Troponin in the sample with a limit of detection of 3 pg/mL.

14. The method of claim 1 further comprising operating the reader to output a Troponin concentration reading.

15. The method of claim 1 wherein the step of operating the reader to detect a reaction further comprises operating the reader to detect the reaction between the reporter antibody and the substrate solution to measure a concentration of Troponin in the whole blood sample with a linear correlation between Troponin concentration and signal over a concentration range of 0-180 pg/ml of Troponin in whole blood.

16. A cartridge for detecting a concentration of Troponin in a whole blood sample, the cartridge comprising:
- a cartridge body adapted to be inserted into a cartridge reader;
- a sample chamber within the cartridge body and comprising an opening for depositing a whole blood sample;
- a detection channel within the cartridge body and communicating with the sample chamber to receive the whole blood sample from the sample chamber in response to actuation by the cartridge reader;
- Troponin reporter antibody amended with an enzyme label disposed in the sample chamber and/or in the detection channel;
- an analyte sensor in the detection channel, the analyte sensor comprising an electrode array, a first electrode of the electrode array comprising a sensor electrode having affixed thereon an anti-Troponin capture antibody;
- a wash liquid disposed in a first reservoir in the cartridge body and communicating with the detection channel;
- a reagent solution disposed in a second reservoir in the cartridge body and communicating with the detection channel; and
- a waste compartment in the cartridge body and communicating with the detection channel;
- the cartridge being operable by the cartridge reader to detect a reaction between the Troponin reporter antibody as amended with the enzyme and the substrate solution to measure a concentration of Troponin in the whole blood sample with a limit of detection of 3 pg/mL.

17. The cartridge of claim 16 wherein the first reservoir is adapted to receive a motive force from the cartridge reader to move wash liquid from the wash liquid reservoir and into a reagent channel.

18. The cartridge of claim 17 wherein the first reservoir comprises a blister pack, the motive force comprising a compressive force applied to the blister pack by the cartridge reader.

19. The cartridge of claim 17 further comprising an inlet in the cartridge body communicating with the reagent channel and adapted to receive a pneumatic force from the cartridge reader to move a portion of the wash liquid from the reagent channel into the detection channel.

20. The cartridge of claim 17 wherein the wash liquid in the first reservoir has a volume equal to or less than a volume of the reagent channel.

21. The cartridge of claim 16 wherein the second reservoir is adapted to receive a motive force from the cartridge reader to move reagent solution into the detection channel.

22. The cartridge of claim 21 wherein the second reservoir comprises a blister pack, the motive force comprising a compressive force applied to the blister pack by the cartridge reader.

23. The cartridge of claim 16 wherein the reagent solution in the second reservoir has a volume greater than a volume of the detection channel.

24. The cartridge of claim 16 wherein the second reservoir communicates with the detection channel at a first point on a first side of the electrode array and the storage chamber communicates with the detection channel at a second point on a second side of the electrode array.

25. The cartridge of claim 24 wherein the waste compartment communicates with the detection channel on the first side of the electrode array.

26. The cartridge of claim 16 wherein a second electrode of the electrode array has a Troponin capture antibody affixed thereon.

27. The cartridge of claim 26 wherein a third a third electrode of the electrode array has an antibody not specific to Troponin affixed thereon.

28. The cartridge of claim 16 wherein the cartridge is further operable by the cartridge reader to detect the reaction between the reporter antibody and the substrate solution to measure a concentration of Troponin in the whole blood sample with a linear correlation between Troponin concentration and signal over a concentration range of 0-180 pg/ml of Troponin in whole blood.

29. The cartridge of claim 16 further comprising an inlet in the cartridge body communicating with the sample chamber and adapted to receive a pneumatic force from the cartridge reader to move the biological sample from the sample chamber into the detection channel.

30. The cartridge of claim 16 further comprising an inlet in the cartridge body communicating with the reagent channel, the second inlet adapted to receive a pneumatic force from the cartridge reader to move wash liquid from the reagent channel into the detection channel.

31. The cartridge of claim 16 further comprising an inlet in the cartridge body communicating with the detection channel and adapted to receive air from the cartridge reader and to permit the air to flow into the detection channel.

* * * * *